United States Patent
Kawai et al.

(10) Patent No.: US 10,605,777 B2
(45) Date of Patent: Mar. 31, 2020

(54) METHOD FOR INSPECTING ELECTROCONDUCTIVE COMPOSITE MATERIAL AND DEVICE FOR INSPECTING ELECTROCONDUCTIVE COMPOSITE MATERIAL

(71) Applicant: IHI Corporation, Koto-ku (JP)

(72) Inventors: Hiroki Kawai, Koto-ku (JP); Akinori Tsuda, Koto-ku (JP); Hiroaki Hatanaka, Koto-ku (JP); Yuichi Yamaguchi, Koto-ku (JP); Koichi Inagaki, Koto-ku (JP)

(73) Assignee: IHI Corporation, Koto-ku (JP)

( * ) Notice: Subject to any disclaimer, the term of this patent is extended or adjusted under 35 U.S.C. 154(b) by 58 days.

(21) Appl. No.: 16/085,384

(22) PCT Filed: Aug. 15, 2016

(86) PCT No.: PCT/JP2016/073832
§ 371 (c)(1),
(2) Date: Sep. 14, 2018

(87) PCT Pub. No.: WO2017/158864
PCT Pub. Date: Sep. 21, 2017

(65) Prior Publication Data
US 2019/0072521 A1 Mar. 7, 2019

(30) Foreign Application Priority Data
Mar. 16, 2016 (JP) .................. 2016-052606

(51) Int. Cl.
*G01N 27/82* (2006.01)
*G01N 27/72* (2006.01)

(52) U.S. Cl.
CPC ............. *G01N 27/82* (2013.01); *G01N 27/72* (2013.01)

(58) Field of Classification Search
CPC .................. G01N 27/82; G01N 27/72; G01N 27/825–87; G01N 27/902; G01M 5/0091
(Continued)

(56) References Cited

U.S. PATENT DOCUMENTS 5,086,274 A * 2/1992 Gobin .................... G01R 27/04
324/230
5,438,262 A * 8/1995 Nanjyo ................ G01N 27/902
324/209
(Continued)

FOREIGN PATENT DOCUMENTS

JP 2-150765 A 6/1990
JP 7-225222 A 8/1995
(Continued)

OTHER PUBLICATIONS

International Search Report dated Nov. 8, 2016, in PCT/JP2016/073832, 2 pages.
(Continued)

*Primary Examiner* — Patrick Assouad
*Assistant Examiner* — Demetrius R Pretlow
(74) *Attorney, Agent, or Firm* — Oblon, McClelland, Maier & Neustadt, L.L.P.

(57) ABSTRACT

Provided is a method for inspecting an electroconductive composite material including disposing a detection magnetic field measurement unit, disposing a correction magnetic field measurement unit, applying a current, acquiring a detection magnetic field strength, acquiring a correction magnetic field strength, and detecting a portion in which arrangement of carbon fibers is disordered. The operation includes calculating a correction coefficient using the correction magnetic field strength and correcting the detection magnetic field strength using the correction coefficient.

5 Claims, 8 Drawing Sheets

(58) Field of Classification Search
USPC .................................................. 324/237–242
See application file for complete search history.

(56) References Cited

U.S. PATENT DOCUMENTS

| | | | | | |
|---|---|---|---|---|---|
| 5,453,291 | A | * | 9/1995 | Sasahara | B29C 70/885 324/237 |
| 5,640,088 | A | * | 6/1997 | Sasahara | G01N 27/72 324/209 |
| 10,088,452 | B2 | * | 10/2018 | Villani, Jr. | G01N 27/82 |
| 2008/0211492 | A1 | * | 9/2008 | Tsukada | G01N 27/72 324/234 |
| 2012/0068696 | A1 | | 3/2012 | Mizutani et al. | |
| 2012/0126803 | A1 | * | 5/2012 | Goldfine | G01N 27/90 324/239 |
| 2015/0301139 | A1 | * | 10/2015 | Shames | G01N 24/08 324/309 |
| 2016/0209365 | A1 | * | 7/2016 | Tsuda | G01M 5/0091 |
| 2017/0292925 | A1 | * | 10/2017 | Zhao | G01N 25/20 |

FOREIGN PATENT DOCUMENTS

| | | |
|---|---|---|
| JP | 7-229875 A | 8/1995 |
| JP | 9-72884 A | 3/1997 |
| JP | 2000-146919 A | 5/2000 |
| JP | 2000-283964 A | 10/2000 |
| JP | 2004-45143 A | 2/2004 |
| JP | 2009-229337 A | 10/2009 |
| JP | 2010-281657 A | 12/2010 |
| JP | 2012-247377 A | 12/2012 |
| JP | 2015-52467 A | 3/2015 |
| JP | 2015-75447 A | 4/2015 |
| RU | 2 312 332 C1 | 12/2007 |
| SU | 1670572 A1 | 8/1991 |
| WO | WO 2015/052956 A1 | 4/2015 |

OTHER PUBLICATIONS

Koichi Mizukami, et al., "Detection of Fiber Waviness in CFRP Using Eddy Current Testing" Symposium on Advanced Materials and Nondestructive Measurements for the Establishment of a Safe and Secure Society Perspectives for Next Generation Sensors for Super-High Temperature Environment and Their Industrial Applications Joint symposium Proceeding. The Japanese Society for Non Destructive Inspection Division of Non-Destructive Evaluation of New Materials. Mar. 2015, pp. 55-60 and cover pages (with English Abstract).

Martin H. Schulze, et al., "High-Resolution Eddy Current Sensor System for Quality Assessment of Carbon Fiber Materials" Microsyst Technol., vol. 16, 2010, pp. 791-797.

* cited by examiner (a)

(b)

(c)

METHOD FOR INSPECTING ELECTROCONDUCTIVE COMPOSITE MATERIAL AND DEVICE FOR INSPECTING ELECTROCONDUCTIVE COMPOSITE MATERIAL

TECHNICAL FIELD

The present disclosure relates to a method for inspecting an electroconductive composite material and a device for inspecting an electroconductive composite material. Priority is claimed on Japanese Patent Application No. 2016-052606, filed Mar. 16, 2016, the content of which is incorporated herein by reference.

BACKGROUND ART

An electroconductive composite material includes a plurality of stacked prepregs. The prepreg is a carbon fiber woven fabric. For example, the electroconductive composite material may be a carbon fiber woven fabric impregnated with a thermosetting resin or a thermoplastic resin. In the prepreg, the carbon fibers in the resin are oriented in a predetermined direction. The arrangement disorder of the carbon fibers influences mechanical properties of the electroconductive composite material. Therefore, an arrangement state of the carbon fibers may be inspected in a manufacturing process of the electroconductive composite material.

When an electroconductive composite material has a form of flat plates, an arrangement disorder of the carbon fibers includes a disorder in a thickness direction (that is, out-of-plane direction) of the electroconductive composite material and a disorder in a direction perpendicular to the thickness direction (that is, in-plane direction). Therefore, in the manufacturing process of an electroconductive composite material, an arrangement disorder in the out-of-plane direction and an arrangement disorder in the in-plane direction are inspected for. For example, an ultrasonic flaw detection method described in Patent Literature 1 may be used for inspection for arrangement disorder in the out-of-plane direction. A method of cutting a flat plate-form electroconductive composite material and observing a cut surface thereof, or a method of finely cutting the electroconductive composite material and detecting the disorder in the carbon fibers using X-rays may be used for inspection for arrangement disorder in the in-plane direction. Further, for the inspection for arrangement disorder in the in-plane direction, for example, a fiber meandering detection method for the electroconductive composite material described in Patent Literature 2 may also be used.

CITATION LIST

Patent Literature

[Patent Literature 1] Japanese Unexamined Patent Publication No. H02-150765
[Patent Literature 2] Japanese Unexamined Patent Publication No. 2015-75447

SUMMARY OF INVENTION

Technical Problem

When electroconductive composite materials are applied in industrial applications such as aircraft parts, excellent mechanical properties may be required for the electroconductive composite materials. Arrangement disorders of the carbon fibers affect the mechanical properties. Accordingly, the present disclosure describes a method and a device for inspecting an electroconductive composite material capable of reliably detecting an arrangement disorder of carbon fibers.

Solution to Problem

One aspect of the present disclosure provides a method for inspecting an electroconductive composite material including carbon fibers, including disposing a first magnetic field measurement unit which acquires a magnetic field strength in a direction along a first detection axis so that the first detection axis is parallel to a set arrangement direction of the carbon fibers at a position facing a main surface of a test specimen including the electroconductive composite material, disposing a second magnetic field measurement unit which acquires a magnetic field strength in a direction along a second detection axis so that the second detection axis is perpendicular to the set arrangement direction of the carbon fibers at the position facing the main surface of the test specimen, applying a current between one end and another end of the test specimen via the carbon fibers, acquiring a first magnetic field strength output from the first magnetic field measurement unit while relatively moving the first magnetic field measurement unit with respect to the main surface, acquiring a second magnetic field strength output from the second magnetic field measurement unit while relatively moving the second magnetic field measurement unit with respect to the main surface, and detecting a portion in which the arrangement of the carbon fibers is disordered using the first magnetic field strength and the second magnetic field strength, wherein the detection of a portion in which the arrangement of the carbon fibers is disordered includes acquiring a correction coefficient which corrects the first magnetic field strength using the second magnetic field strength, acquiring a corrected first magnetic field strength using the correction coefficient, and detecting a portion in which the arrangement of the carbon fibers is disordered using the corrected first magnetic field strength.

Effects of Invention

According to the method and the device for inspecting an electroconductive composite material of the present disclosure, it is possible to reliably detect arrangement disorder of the carbon fibers.

DESCRIPTION OF EMBODIMENTS

Figure 1:
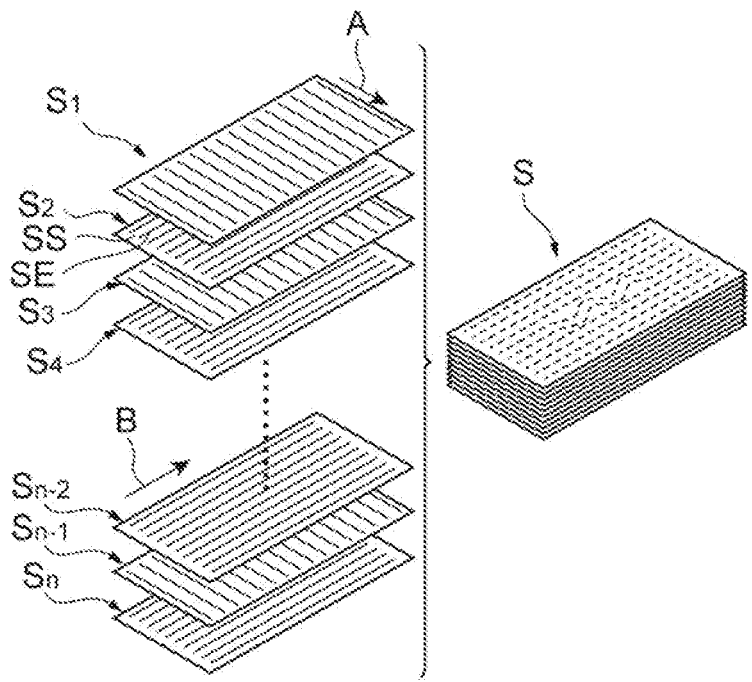
FIG. 1(a) is a perspective view illustrating a structure of an electroconductive composite material inspected by a method for inspecting an electroconductive composite material according to the present disclosure.
FIG. 1(b) and FIG. 1(c) are perspective views illustrating meandering that may occur in the electroconductive composite material.
Figure 1:
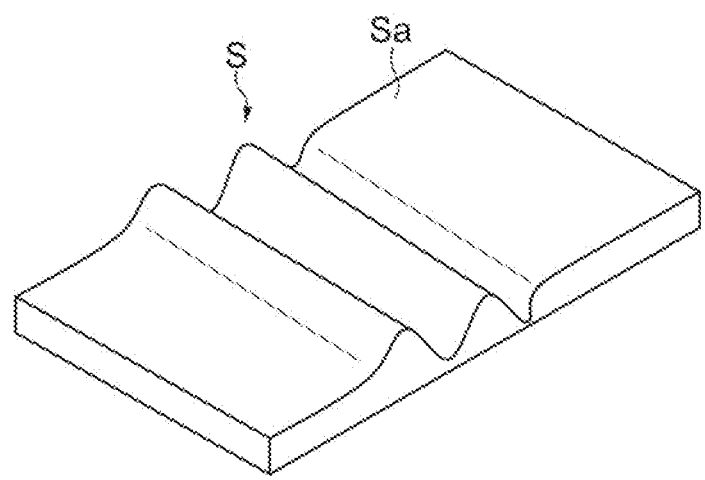
Figure 1:
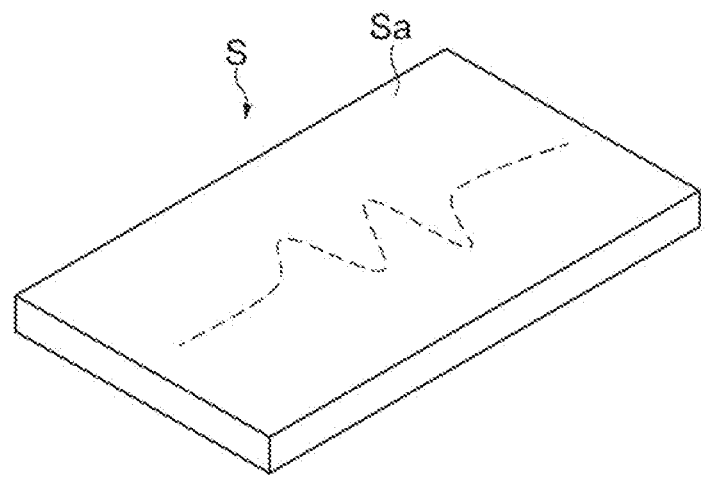

One aspect of the present disclosure is a method for inspecting an electroconductive composite material including carbon fibers, including a step of disposing a first magnetic field measurement unit which acquires a magnetic field strength in a direction along a first detection axis so that the first detection axis is parallel to a set arrangement direction of the carbon fibers at a position facing a main surface of a test specimen including the electroconductive composite material, a step of disposing a second magnetic field measurement unit which acquires a magnetic field strength in a direction along a second detection axis so that the second detection axis intersects the set arrangement direction of the carbon fibers at a position facing the main surface of the test specimen, a step of applying a current between one end and another end of the test specimen via the carbon fibers, a step of acquiring a first magnetic field strength output from the first magnetic field measurement unit while relatively moving the first magnetic field measurement unit with respect to the main surface, a step of acquiring a second magnetic field strength output from the second magnetic field measurement unit while relatively moving the second magnetic field measurement unit with respect to the main surface, and a step of detecting a portion in which the arrangement of the carbon fibers is disordered using the first magnetic field strength and the second magnetic field strength, wherein the step of detecting a portion in which the arrangement of the carbon fibers is disordered includes a step of acquiring a correction coefficient which corrects the first magnetic field strength using the second magnetic field strength, a step of acquiring a corrected first magnetic field strength using the correction coefficient, and a step of detecting a portion in which the arrangement of the carbon fibers is disordered using the corrected first magnetic field strength.

The arrangement of the carbon fibers may deviate from a preset arrangement direction. In this way, a state in which an actual arrangement direction of the carbon fibers deviates from the set arrangement direction is assumed to be a state in which the arrangement of the carbon fibers is disordered. In the step of applying the current, when the current is applied through the carbon fibers, a magnetic field is generated. The magnetic field is orthogonal to a direction in which the current flows. Since the current flows through the carbon fibers, the direction in which the current flows coincides with the actual arrangement direction of the carbon fibers. Therefore, the magnetic field is orthogonal to the actual arrangement direction of the carbon fibers. When the actual arrangement direction of the carbon fibers deviates from the set arrangement direction, a direction of the magnetic field is inclined at an angle which is not orthogonal to the set arrangement direction. The magnetic field strength is affected by the current value.

Since the first magnetic field measurement unit is disposed so that the first detection axis is parallel to the set arrangement direction, the first magnetic field strength in the set arrangement direction is acquired. When there is no arrangement disorder of the carbon fibers, the magnetic field is orthogonal to the set arrangement direction. Therefore, the first magnetic field strength is zero. On the other hand, when the arrangement of the carbon fibers is disordered, the magnetic field is inclined with respect to the set arrangement direction, and thus the first magnetic field strength is a predetermined value. That is, according to the step of acquiring the first magnetic field strength, the first magnetic field strength including an influence due to a arrangement disorder of the carbon fibers and an influence of the current value is obtained.

In some aspects, the second magnetic field measurement unit is disposed so that the second detection axis intersects the set arrangement direction. Therefore, the second magnetic field measurement unit acquires a second magnetic field strength in a direction perpendicular to the set arrangement direction. The second magnetic field strength is proportional to the current value. That is, according to the step of acquiring the second magnetic field strength, the second magnetic field strength including an influence of the current value is obtained.

Additionally, in the step of detecting a portion in which the carbon fibers are disordered, first, the correction coefficient is acquired using the second magnetic field strength. The correction coefficient reduces the influence of the current value included in the first magnetic field strength. Therefore, the influence of the current value included in the first magnetic field strength is reduced by correcting the first magnetic field strength using the correction coefficient. Thus, according to the step of detecting a portion in which the arrangement of the carbon fibers is disordered using the corrected first magnetic field strength, it is possible to reliably detect arrangement disorder of the carbon fibers.

In some aspects, the step of acquiring the correction coefficient may include a step of obtaining an average value of the second magnetic field strength, and a step of calculating the correction coefficient using the second magnetic field strength and the average value. According to the step, a suitable correction coefficient can be obtained.

In some aspects, in the step of acquiring the corrected first magnetic field strength, the first magnetic field strength may be divided by the correction coefficient. According to the step, it is possible to suitably obtain the first magnetic field strength excluding the influence of the current value.

Another aspect of the present disclosure is a device for inspecting an electroconductive composite material including carbon fibers, including a first magnetic field measurement unit configured to acquire a magnetic field strength in a direction along a first detection axis and disposed so that the first detection axis is parallel to a set arrangement direction of the carbon fibers at a position facing a main surface of a test specimen including the electroconductive composite material, a second magnetic field measurement unit configured to acquire a magnetic field strength in a direction along the second detection axis and disposed so that the second detection axis intersects the set arrangement direction of the carbon fibers at the position facing the main surface of the test specimen, a current applying unit configured to apply a current between one end and another end of the test specimen via the carbon fibers, a moving mechanism unit configured to relatively move the first magnetic field measurement unit and the second magnetic field measurement unit with respect to the main surface, and a data processing unit configured to detect a portion in which arrangement of the carbon fibers is disordered using the first magnetic field strength output from the first magnetic field measurement unit and the second magnetic field strength output from the second magnetic field measurement unit, wherein the data processing unit includes a correction coefficient acquisition unit configured to acquire a correction coefficient which corrects the first magnetic field strength using the second magnetic field strength, a signal correction unit configured to acquire a corrected first magnetic field strength using the correction coefficient, and a meandering inspection unit configured to detect a portion in which the arrangement of the carbon fibers is disordered using the corrected first magnetic field strength. According to the device, like in the above-described inspection method, the first magnetic field strength excluding the influence of the current value is obtained. Therefore, it is possible to reliably detect arrangement disorder of the carbon fibers.

Hereinafter, means for implementing the present disclosure will be described in detail with reference to the accompanying drawings. In the description of the drawings, the same elements are designated by the same reference numerals, and repeated descriptions are omitted.

As illustrated in FIG. 1(a), a method and a device for inspecting an electroconductive composite material according to the present disclosure are used for inspecting a test specimen S. The test specimen S has a rectangular parallelepiped shape in which a plurality of prepregs (S1, S3, . . . , Sn–1) and (S2, S4, . . . Sn–2, Sn) are stacked. Each of the prepregs is obtained by impregnating an carbon fiber woven fabric SS with a thermoplastic resin or a thermosetting resin. In the test specimen S, arrangement directions of carbon fibers SE included in the prepreg differ from each other by 90°. Therefore, the test specimen S has two arrangement directions.

In the following description, the terms "set arrangement direction" and "actual arrangement direction" are used with respect to the arrangement direction. The "set arrangement direction" is a preset direction and is always constant. On the other hand, the "actual arrangement direction" is a direction in which the carbon fibers SE are actually oriented and is distinguished from the set arrangement direction. "Arrangement disorder" and "meandering" mean that the actual arrangement direction is not parallel to the set arrangement direction. That is, "arrangement disorder" and "meandering" refer to a state in which the actual arrangement direction is inclined and intersects the set arrangement direction.

In a prepreg material, the carbon fibers SE are oriented in a predetermined direction. The arrangement of the carbon fibers SE may change due to heating or cooling in a molding process. A state in which the arrangement of the carbon fibers SE has changed is called a arrangement disorder of the fibers or meandering of the fibers. As illustrated in FIG. 1(b) and FIG. 1(c), meandering of the fibers may be in two forms. Meandering of the fibers includes meandering (refer to FIG. 1(b)) in a thickness direction of the test specimen S, and meandering (refer to FIG. 1(c)) along a main surface Sa of the test specimen S. In the inspection method and the inspection device of the present disclosure, the meandering illustrated in FIG. 1(c) is a target of the inspection.

Figure 2:
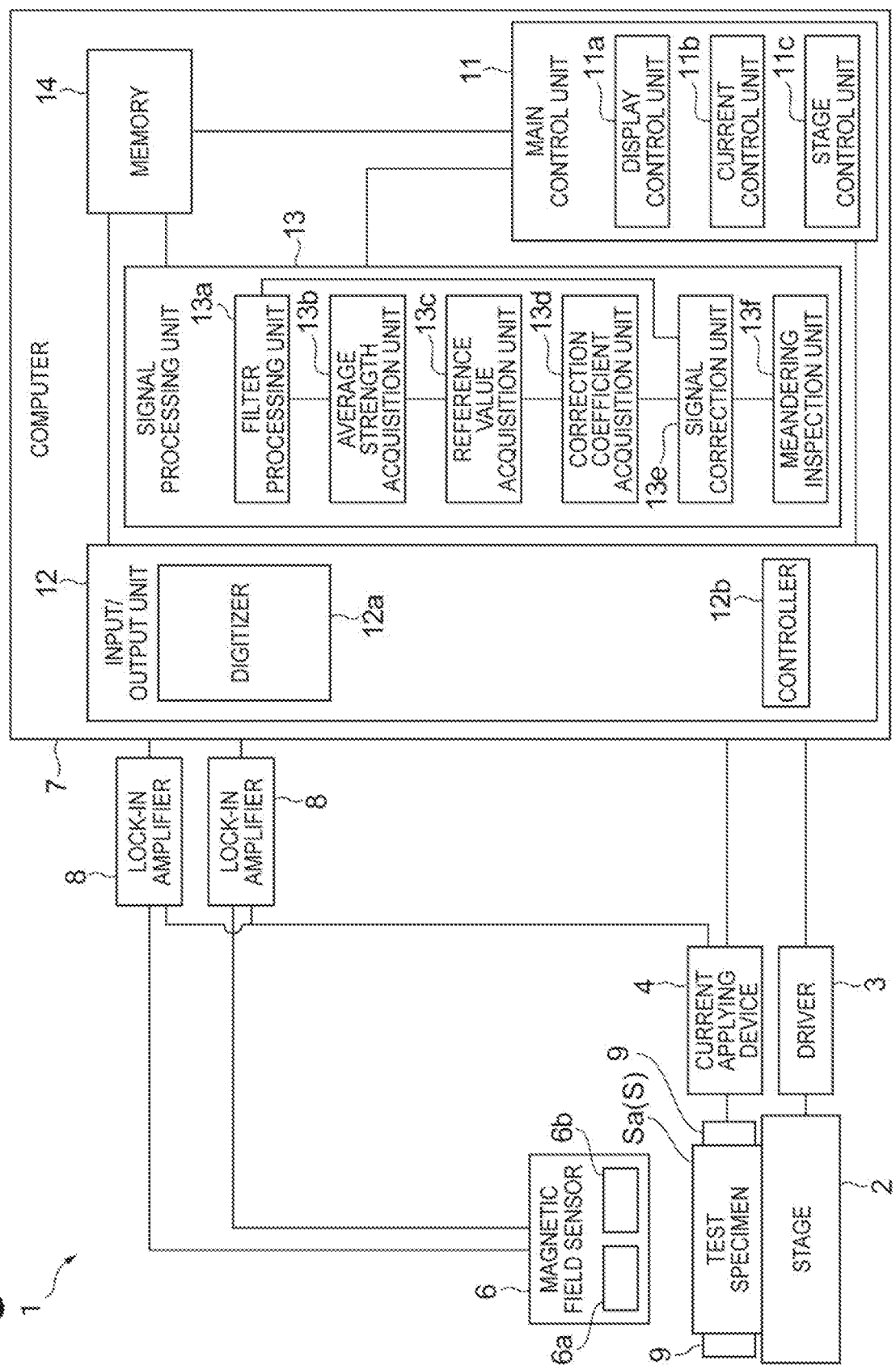
FIG. 2 is a block diagram illustrating a configuration of a device for inspecting an electroconductive composite material which performs the method for inspecting an electroconductive composite material according to the present disclosure.

A fiber meandering inspection device used in the method for inspecting an electroconductive composite material will be described. As illustrated in FIG. 2, the fiber meandering inspection device 1 (device for inspecting an electroconductive composite material) includes a stage 2 (moving mechanism unit), a driver 3, a current applying device 4 (current applying unit), a magnetic field sensor 6, and a computer 7 (data processing unit). The fiber meandering inspection device 1 may include a desired device (for example, a lock-in amplifier 8) necessary for processing a signal output from the magnetic field sensor 6. The lock-in amplifier 8 uses an output of the current applying device 4 as a reference signal and detects an output of the magnetic field sensor 6. In the lock-in amplifier 8, a phase of an output of the magnetic field sensor 6 with respect to a phase of an output signal of the current applying device 4 is adjusted so that a detection signal input to the computer 7 is maximized.

The stage 2 as the moving mechanism unit relatively moves the magnetic field sensor 6 with respect to the main surface Sa of the test specimen S. The stage 2 is a two-axis stage. Two movement axes of the stage 2 form a plane parallel to the main surface Sa. In the fiber meandering inspection device 1 of the present disclosure, the magnetic field sensor 6 is fixed, and the test specimen S is moved with respect to the magnetic field sensor 6. The moving mechanism unit may have a configuration in which the test specimen S is fixed and the magnetic field sensor 6 is moved with respect to the test specimen S. An operation of the stage 2 is controlled by a control signal input from the driver 3. The driver 3 is connected to the stage 2 and the computer 7. The driver 3 generates a signal for controlling the operation of the stage 2 on the basis of a control signal input from the computer 7.

The current applying device 4 is connected to the test specimen S, the computer 7 and the lock-in amplifier 8. The current applying device 4 applies a current to the test specimen S. For example, it is assumed that a plurality of prepregs S2, S4, . . . , Sn are inspection targets in a plurality of prepregs S1 to Sn constituting the test specimen S. The prepregs S2, S4, . . . , Sn have a set arrangement direction B. In this case, the current applying device 4 applies a current in the set arrangement direction B of the carbon fibers SE in the plurality of prepregs S2, S4, . . . , Sn. The current applying device 4 has a pair of electrodes 9. When the plurality of prepregs S2, S4, . . . , Sn are the inspection targets, the electrodes 9 are installed at end portions of the test specimen S intersecting the set arrangement direction B of the prepregs S2, S4, . . . , Sn.

As illustrated in FIG. 3(a), the magnetic field sensor 6 is disposed on the main surface Sa of the specimen S. The magnetic field sensor 6 acquires a magnetic field strength. The magnetic field sensor 6 has a detection magnetic field measurement unit 6a (first magnetic field measurement unit) and a correction magnetic field measurement unit 6b (second magnetic field measurement unit). The detection magnetic field measurement unit 6a acquires a magnetic field strength in a direction of a first detection axis D1. The correction magnetic field measurement unit 6b acquires a magnetic field strength in a direction of a second detection axis D2. The magnetic field sensor 6 has two detection axes (the first detection axis D1 and the second detection axis D2). The magnetic field sensor 6 outputs a signal corresponding to the magnetic field strength in the direction of the detection axis as a voltage value to the lock-in amplifier 8. For the magnetic field sensor 6, a magneto-impedance (MI) sensor, a giant magneto-resistance (GMR) sensor, a tunnel magneto-resistance (TMR) sensor, an anisotropic magneto-resistance (AMR) sensor, a flux gate (FG) sensor, a Hall element, a superconducting quantum interference device (SQUID) sensor, a coil and so on can be adopted.

When a current E is supplied to the test specimen S, the current E flows between one end and another end of the specimen S via the carbon fibers SE. A magnetic field M is generated by the current E. Therefore, an output of the magnetic field sensor 6 is influenced by a current value caused by the current E. A direction of the magnetic field M is orthogonal to a direction of the current E. In other words, the direction of the magnetic field M is orthogonal to the actual arrangement direction C in which the carbon fibers SE are arranged. When the actual arrangement direction C deviates from the set arrangement direction B (refer to FIG. 3(b)), the direction of the magnetic field M is not orthogonal to the set arrangement direction B. In other words, when the carbon fibers SE meander, the direction of the magnetic field M is not orthogonal to the set arrangement direction B. Therefore, the direction of the magnetic field M is inclined with respect to the set arrangement direction B. Additionally, the output of the magnetic field sensor 6 is influenced by the actual arrangement direction C. In other words, the output of the magnetic field sensor 6 includes an influence of the current value of the current E and an influence of the actual arrangement direction C.

The computer 7 will be described with reference to FIG. 2. The computer 7 includes a main control unit 11, an input/output unit 12, a signal processing unit 13, and a memory 14. The computer 7 controls an operation of the stage 2 and an operation of the current applying device 4. The computer 7 inspects for meandering using an output signal of the magnetic field sensor 6. The computer 7 is connected to the driver 3, the current applying device 4, and the lock-in amplifier 8.

The main control unit 11 controls the entire operation of the computer 7. The main control unit 11 displays processing results of the signal processing unit 13. The main control unit 11 controls the operation of the stage 2 and the operation of the current applying device 4. The main control unit 11 is connected to the input/output unit 12 and outputs a control signal to the input/output unit 12. The main control unit 11 is connected to the signal processing unit 13 and receives a processing signal from the signal processing unit 13. The main control unit 11 is connected to the memory 14 and reads various setting values and so on stored in the memory 14. The main control unit 11 includes a display control unit 11a, a current control unit 11b, and a stage control unit 11c. The display control unit 11a, the current control unit 11b, and the stage control unit 11c are functional elements realized by executing a program stored in the memory 14 of the computer 7 with a CPU or the like. The display control unit 11a is connected to the signal processing unit 13 and causes the display device such as a display to display the processing signal received from the signal processing unit 13. The current control unit 11b is connected to the input/output unit 12 and outputs a control signal for controlling the operation of the current applying device 4 to the input/output unit 12. The control signal of the current control unit 11b controls, for example, starting and stopping of current application and a frequency or a current value of the current E output from the current applying device 4. The stage control unit 11c is connected to the input/output unit 12 and outputs a control signal for controlling the operation of the stage 2 to the input/output unit 12. The stage control unit 11c outputs position information of the stage 2 using this control signal. The position information may be generated by another element. A specific operation of the stage 2 will be described later.

The input/output unit 12 receives a signal input from a device such as the lock-in amplifier 8. The input/output unit 12 outputs a signal for controlling an operation of devices such as the driver 3 and the current applying device 4. The input/output unit 12 is connected to the driver 3, the current applying device 4, and the lock-in amplifier 8. The input/output unit 12 includes a digitizer 12a and a controller 12b. The digitizer 12a which is a so-called analog-to-digital converter is connected to the lock-in amplifier 8, the signal processing unit 13 and the memory 14. The digitizer 12a converts an analog signal input from the lock-in amplifier 8 into a digital signal. The digitizer 12a outputs the digital signal to the signal processing unit 13 or the memory 14. The controller 12b is connected to the driver 3 and the main control unit 11. The controller 12b generates a control signal to be provided to the driver 3 using a control signal provided from the main control unit 11. The controller 12b outputs a control signal to the driver 3.

The signal processing unit 13 is connected to the main control unit 11, the input/output unit 12, and the memory 14. The signal processing unit 13 inspects for meandering using information input from the input/output unit 12 or information read from the memory 14. The inspection related to meandering includes an inspection related to the presence or absence of meandering, an inspection related to a degree of meandering, and so on. For example, the signal processing unit 13 determines the presence or absence of meandering. When it is determined that meandering is present, the signal processing unit 13 calculates quantitatively the degree of meandering. The signal processing unit 13 may determine whether meandering is acceptable using an amount indicating the degree of meandering.

The signal processing unit 13 includes a filter processing unit 13a, an average strength acquisition unit 13b, a reference value acquisition unit 13c, a correction coefficient acquisition unit 13d, a signal correction unit 13e, and a meandering inspection unit 13f. The filter processing unit 13a, the average strength acquisition unit 13b, the reference value acquisition unit 13c, the correction coefficient acquisition unit 13d, the signal correction unit 13e, and the meandering inspection unit 13f are functional elements realized by executing a program stored in the memory 14 of the computer 7 with a CPU or the like.

The filter processing unit 13a is connected to the digitizer 12a of the input/output unit 12, the average strength acquisition unit 13b, the signal correction unit 13e, and the memory 14. The filter processing unit 13a performs desired filter processing (for example, band pass filter processing) on the digital signal input from the digitizer 12a or the information read from the memory 14. The filtered signal is output to the average strength acquisition unit 13b and the signal correction unit 13e.

The average strength acquisition unit 13b is connected to the filter processing unit 13a and the reference value acquisition unit 13c. The average strength acquisition unit 13b calculates a plurality of average strengths using the filtered signal and outputs the average strengths to the reference value acquisition unit 13c. A specific operation of the average strength acquisition unit 13b will be described later.

The reference value acquisition unit 13c is connected to the average strength acquisition unit 13b and the correction coefficient acquisition unit 13d. The reference value acquisition unit 13c selects a reference value from the plurality of average strengths and outputs the reference value to the correction coefficient acquisition unit 13d. A specific operation of the reference value acquisition unit 13c will be described later.

The correction coefficient acquisition unit 13d is connected to the reference value acquisition unit 13c and the signal correction unit 13e. The correction coefficient acquisition unit 13d calculates a correction coefficient using the reference value and the average strength and outputs the correction coefficient to the signal correction unit 13e. A specific operation of the correction coefficient acquisition unit 13d will be described later.

The signal correction unit 13e is connected to the filter processing unit 13a, the correction coefficient acquisition unit 13d, and the meandering inspection unit 13f. The signal correction unit 13e corrects a magnetic field strength input from the filter processing unit 13a using the correction coefficient input from the correction coefficient acquisition unit 13d and outputs the corrected magnetic field strength to the meandering inspection unit 13f. An operation of the signal correction unit 13e will be described later.

The meandering inspection unit 13f is connected to the signal correction unit 13e. The meandering inspection unit 13f performs processing for obtaining the presence or absence of meandering and the degree of meandering using the corrected magnetic field strength input from the signal correction unit 13e. The meandering inspection unit 13f outputs processing results to the main control unit 11 and the memory 14.

The memory 14 stores various setting values and a variety of data used for meandering detection processing. The variety of data used for the meandering detection processing may include information on the acquired magnetic field strength and a correction coefficient. The memory 14 is configured to be readable and writable from the main control unit 11, the input/output unit 12, and the signal processing unit 13. The memory 14 stores the information on the magnetic field strength in association with information on the position of the stage 2 with respect to the magnetic field sensor 6. The information on the magnetic field strength is output from the digitizer 12a of the input/output unit 12. The position information is information indicating a positional relationship between the stage 2 and the magnetic field sensor 6 outputted from the stage control unit 11c of the main control unit 11. The association between the information on the magnetic field strength and the position information may be performed in an element different from the memory 14.

A meandering inspection method using the fiber meandering inspection device 1 will be described. Hereinafter, the principle of the inspection method followed by detailed operation thereof will be described.

Figure 3:
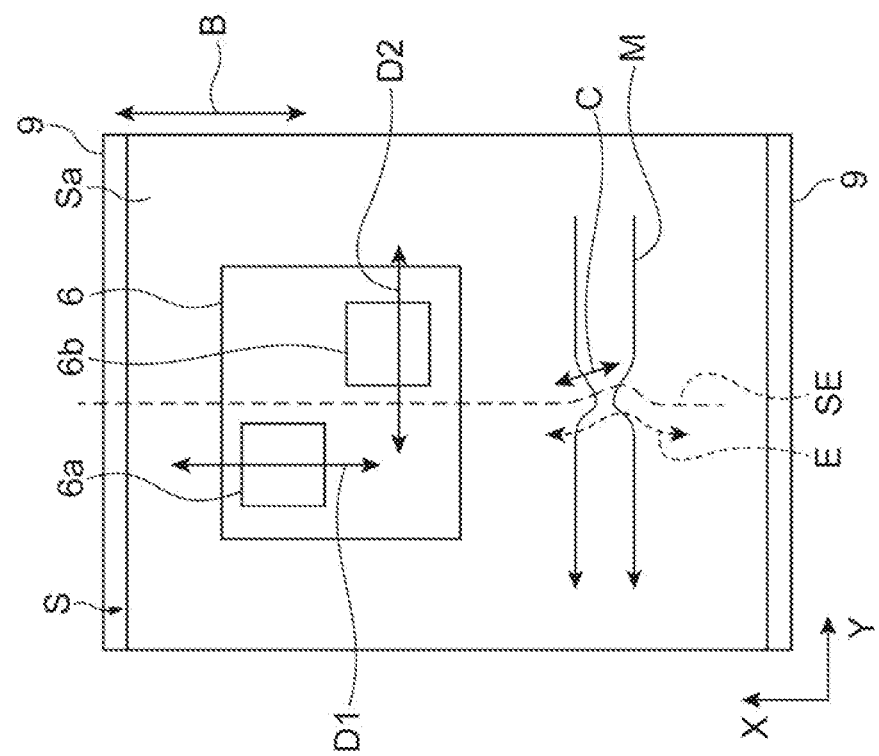
FIG. 3(a) and FIG. 3(b) are diagrams illustrating a relationship between a magnetic field sensor and carbon fibers and a relationship between the magnetic field sensor and a magnetic field.
Figure 3:
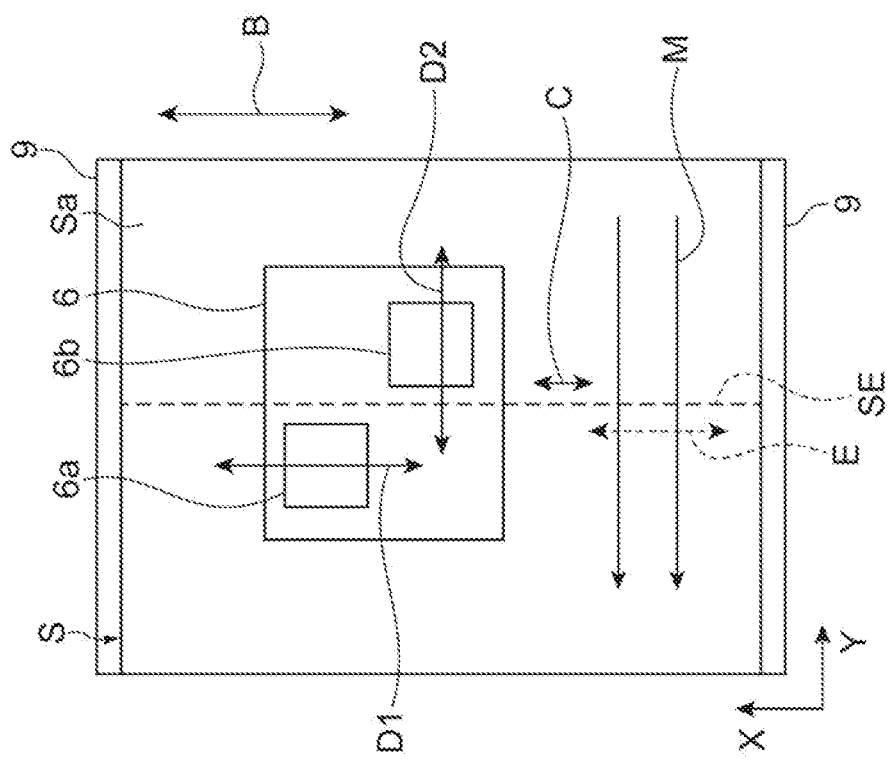

As illustrated in FIG. 3, when the current E is applied to the test specimen S via the electrodes 9 installed on the test specimen S, the electrical current E flows in the actual arrangement direction C through the carbon fibers SE. At this time, a magnetic field M in a direction orthogonal to a direction in which the current E flows is generated. As illustrated in FIG. 3(a), when meandering of the carbon fibers SE does not occur, the actual arrangement direction C and the set arrangement direction B coincide with each other. Therefore, the direction of the magnetic field M is orthogonal to the set arrangement direction B. In this case, a detected magnetic field strength M1 which is an output of the detection magnetic field measurement unit 6a is constant (zero). On the other hand, as illustrated in FIG. 3(b), when meandering occurs in the carbon fibers SE, the actual arrangement direction C and the set arrangement direction B do not coincide. Therefore, an angle between the set arrangement direction B and the magnetic field M changes. That is, since the magnetic field M in a direction corresponding to meandering is generated, the detection magnetic field strength (M1) changes.

The detection magnetic field strength (M1) is influenced by the current value. That is, as the current value increases, the detection magnetic field strength (M1) also increases. On the other hand, as the current value decreases, the detection magnetic field strength (M1) also decreases. Therefore, the detection magnetic field strength (M1) includes an influence of the current value and an influence of the direction in which the carbon fibers SE are arranged (the actual arrangement direction C). The actual arrangement direction C is a main item to be inspected for in the inspection method of the present disclosure.

Figure 4:
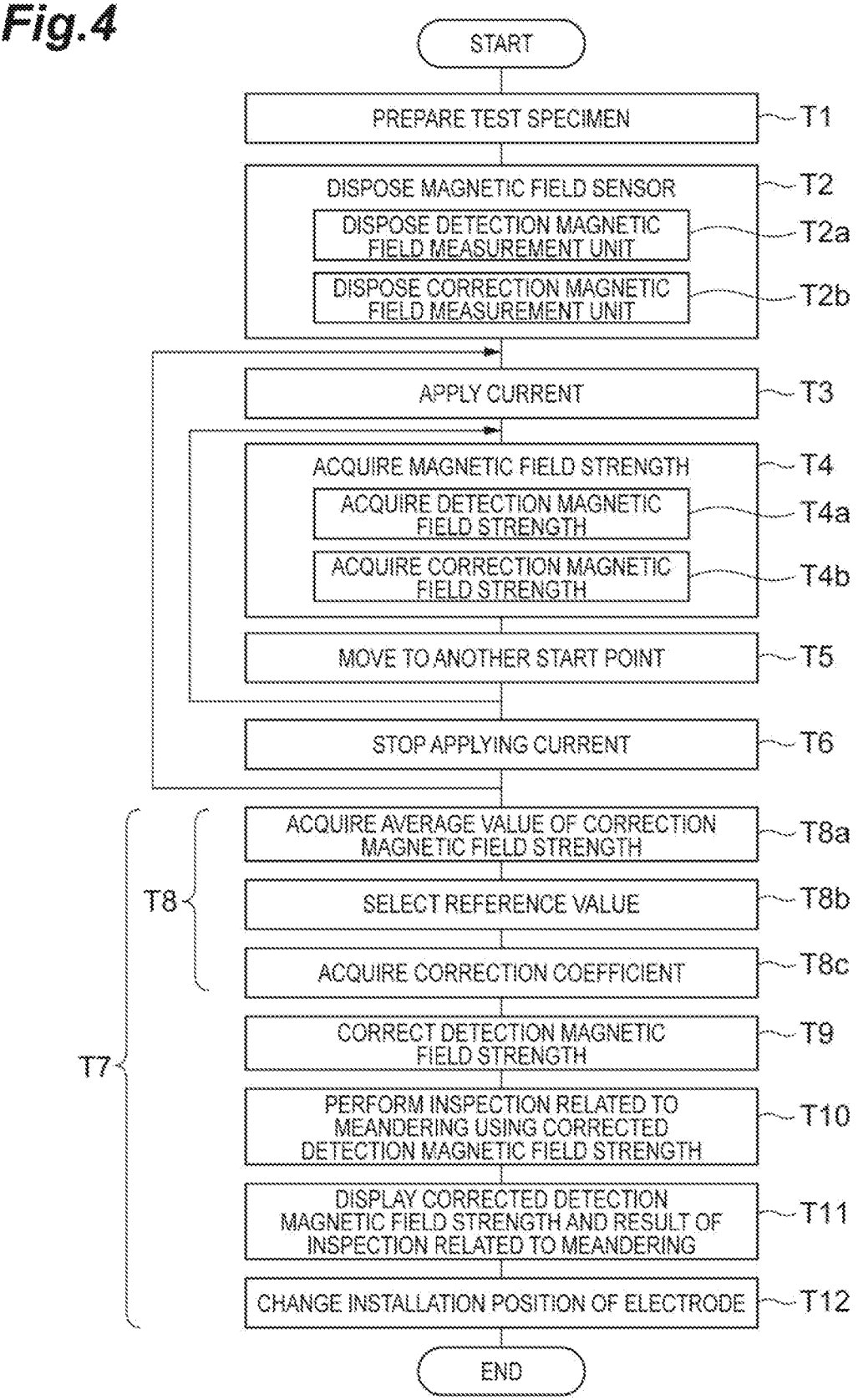
FIG. 4 is a flowchart illustrating main processes of the method for inspecting an electroconductive composite material according to the present disclosure.

Hereinafter, the inspection method according to the present disclosure will be described in more detail with reference to a flowchart illustrated in FIG. 4.

Step T1 of preparing the test specimen S is performed. In Step T1, the electrodes 9 are installed on the test specimen S. The electrodes 9 are installed on each of one end Sb and another end Sc intersecting the set arrangement direction B (refer to FIG. 5). A width of the electrode 9 is empirically decided in consideration of detectability of meandering and workability and so on. As an example, the width of the electrode 9 may be decided from the viewpoint of suppressing a decrease in density of the current E flowing through the test specimen S. For example, when a length of one end Sb is 300 mm, a length of the electrode 9 may be 100 mm. When the length of one end Sb is 600 mm, the length of the electrode 9 may be 100 mm. The test specimen S on which the electrodes 9 are installed is disposed on the stage 2.

Step T2 of disposing the magnetic field sensor 6 is performed. The magnetic field sensor 6 includes the detection magnetic field measurement unit 6a and the correction magnetic field measurement unit 6b. Therefore, Step T2 includes Step T2a of disposing the detection magnetic field measurement unit 6a and Step T2b of disposing the correction magnetic field measurement unit 6b.

Specifically, the magnetic field sensor 6 is disposed at a position facing the main surface Sa of the test specimen S. The magnetic field sensor 6 may be brought into contact with the main surface Sa or may be separated from the main surface Sa by a predetermined distance. In the case of being separated therefrom, for example, a distance between the magnetic field sensor 6 and the main surface Sa is 5 mm or less. The first detection axis D1 is parallel to the set arrangement direction B. The second detection axis D2 is orthogonal to the set arrangement direction B (refer to FIG. 3(a)). In the magnetic field sensor 6, the first detection axis DL and the second detection axis D2 are orthogonal to each other. Therefore, when the first detection axis D1 is disposed to be parallel to the set arrangement direction B, the second detection axis D2 is inevitably disposed to be orthogonal to the set arrangement direction B.

Step T3 of applying the current E is performed. The current E is applied to the test specimen S continuously until a step T6 of stopping the current E which will be performed later. Step T3 is performed by the current applying device 4 and the current control unit 11b of the computer 7. The computer 7 outputs a control signal to operate the current applying device 4. The control signal includes an instruction to start an output of the current E from the current applying device 4. The control signal includes an instruction related to the frequency of the current E and an intensity of the current E. For example, the control signal includes an instruction to set the frequency of the current E to 100 kHz and an instruction to set the intensity of the current E to 200 mA. By performing Step T3, the current E is applied between one end Sb and another end Sc of the test specimen S via the carbon fibers SE. The magnetic field M due to the applied current E is generated.

Figure 5:
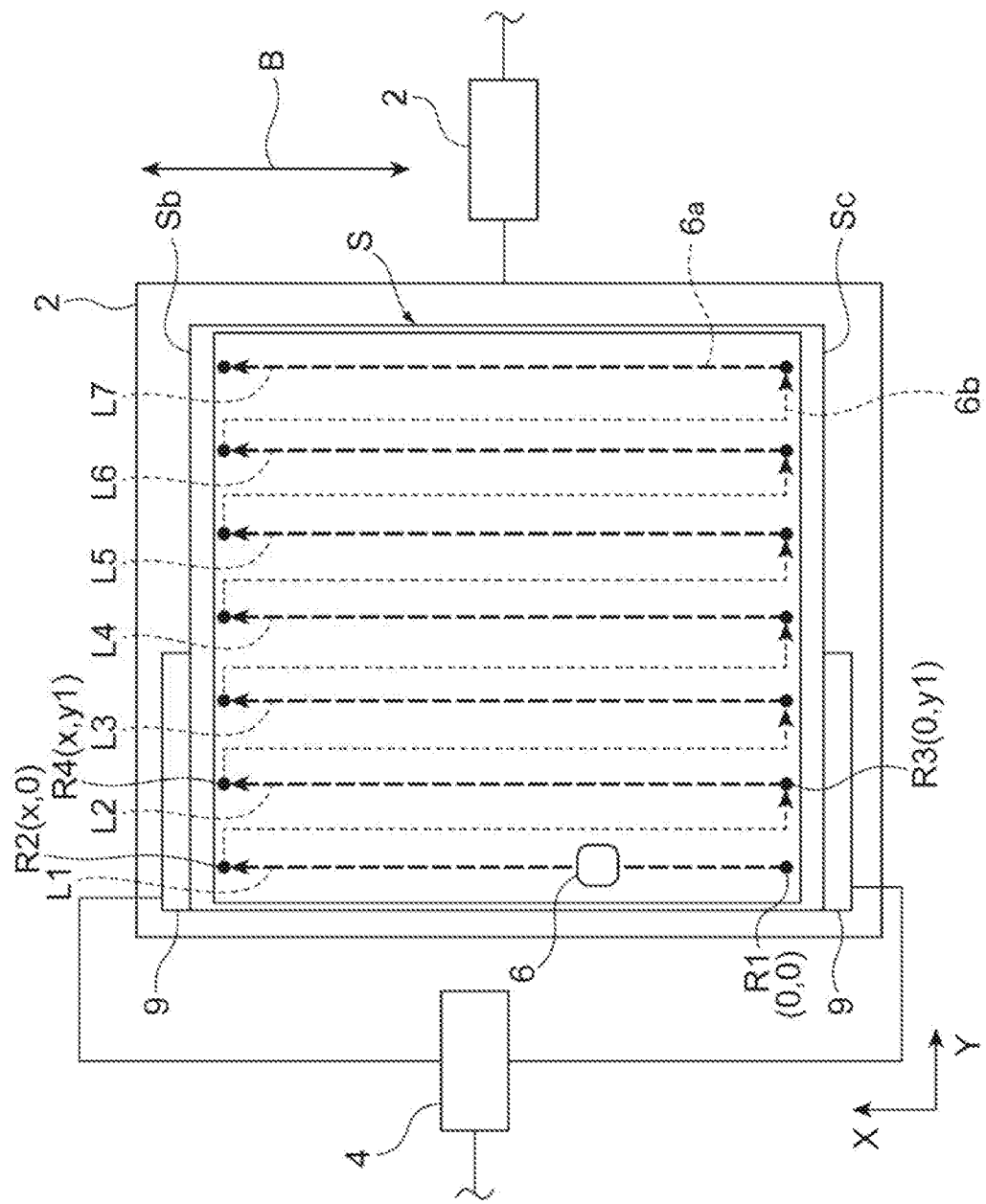
FIG. 5 is a diagram illustrating a positional relationship between a test specimen and a magnetic field sensor.

Step T4 of acquiring the magnetic field strength is performed. In Step T4, as illustrated in FIG. 5, data on the magnetic field strength is acquired while the position of the magnetic field sensor 6 with respect to the test specimen S is relatively moved. The data on the magnetic field strength includes two-dimensional position information (x, y) of the magnetic field sensor 6 with respect to the test specimen S and information on the magnetic field strength at that position. The information on the magnetic field strength includes the detection magnetic field strength (M1) (first magnetic field strength) and the correction magnetic field strength (M2) (second magnetic field strength). For example, the data on the magnetic field strength is a collection of information such as a fact that "when the magnetic field sensor 6 is at a position (x, y) on the main surface Sa of the test specimen S, the detection magnetic field strength (M1) is a value (V1) and the correction magnetic field strength (M2) is a value (V2)".

In Step T4, movement of the test specimen S is performed by the stage 2, the driver 3, the stage control unit 11c, and the controller 12b. In Step T4, acquisition of the data on the magnetic field strength is performed by the magnetic field sensor 6, the lock-in amplifier 8, the digitizer 12a, the filter processing unit 13a, and the memory 14. The stage control unit 11c outputs a control signal for controlling the stage 2 such that the test specimen S is moved along a preset movement course. The control signal is output to the stage 2 via the controller 12b and the driver 3. The stage 2 moves the test specimen S in an X-axis direction and a Y-axis direction according to the control signal.

As illustrated in FIG. 5, specifically, the computer 7 controls the stage 2 so that the magnetic field sensor 6 is disposed at a corner of the test specimen S. Here, this point is called a first start point R1. The first start point R1 is indicated by coordinate information (0, 0). Next, the computer 7 controls the stage 2 so that the magnetic field sensor 6 moves in the X-axis direction from the first start point R1 to a first end point R2. The first end point R2 is indicated by coordinate information (X, 0). While the stage 2 is controlled, the magnetic field sensor 6 outputs the detection magnetic field strength (M1) and the correction magnetic field strength (M2) to the lock-in amplifier 8. At the same time, the stage control unit 11c outputs position information indicating the position of the magnetic field sensor 6 with respect to the stage 2 to the memory 14 on the basis of the control signal. Additionally, the memory 14 of the computer 7 stores the position information (x, y) and the detection magnetic field strength (M1) in association with each other. The memory 14 stores the position information (x, y) and the correction magnetic field strength (M2) in association with each other. Through Step T4, the detection magnetic field strength (M1) and the correction magnetic field strength (M2) along a line L1 are obtained (Steps T4a and T4b).

The computer 7 performs Step T5. In Step T5, the computer 7 controls the stage 2 so that the magnetic field sensor 6 moves from the first end point R2 to a second start point R3. The second start point R3 is indicated by coordinate information (0, y1). When the magnetic field sensor 6 moves from the first end point R2 to the second start point R3, the magnetic field strength output from the magnetic field sensor 6 may be stored in the memory 14 in association with the position information.

The computer 7 performs Step T4 again. The computer 7 controls the stage 2 so that the magnetic field sensor 6 moves in the X-axis direction from the second start point R3 to a second end point R4. The second end point R4 is indicated by coordinate information (X, y1). While the magnetic field sensor 6 moves from the second start point R3 to the second end point R4, the magnetic field sensor 6, the lock-in amplifier 8, the digitizer 12a, the filter processing unit 13a, and the memory 14 perform an operation for acquiring the data on the magnetic field strength. Through Step T4, the detection magnetic field strength (M1) and the correction magnetic field strength (M2) along a line L2 are obtained.

As described above, by repeatedly performing Step T4 and Step T5, the detection magnetic field strength (M1) and the correction magnetic field strength (M2) along each of lines L1, L2, L3, L4, L5, L6 and L7 as the data on the magnetic field strength are obtained.

A relationship between the detection magnetic field strength (M1) and the correction magnetic field strength (M2) will be described. The first detection axis D1 is along the main surface Sa and is parallel to the set arrangement direction B. Therefore, when the direction in which the carbon fibers SE are arranged coincides with the set arrangement direction B, the detection magnetic field strength (M1) is zero. In other words, when the actual arrangement direction C and the set arrangement direction B are coincide with each other, the detection magnetic field strength (M1) is zero. In other words, when the carbon fibers SE meander, the detection magnetic field strength (M1) is a predetermined value which is not zero.

The second detection axis D2 is orthogonal to the first detection axis D1. That is, the second detection axis D2 is along the main surface Sa and is orthogonal to the set arrangement direction B. Therefore, when the actual arrangement direction C coincides with the set arrangement direction B, the correction magnetic field strength (M2) is a predetermined value which is not zero. In other words, when the carbon fibers SE do not meander, the correction magnetic field strength (M2) is a predetermined value which is not zero. On the other hand, when the actual arrangement direction C does not coincide with the set arrangement direction B, the correction magnetic field strength (M2) decreases to a value smaller than the predetermined value. In other words, when the carbon fibers SE meander, the correction magnetic field strength (M2) decreases to a value smaller than the predetermined value.

Step T7 is performed. In Step T7, a portion in which the arrangement of the carbon fibers SE is disordered (meandering portion) is detected using the data on the magnetic field strength. Step T7 includes Step T8 of acquiring the correction coefficient, Step T9 of correcting the detection magnetic field strength (M1) using the correction coefficient, and Step T10 of determining the presence or absence of meandering.

Step T8 of acquiring the correction coefficient will be described. Step T8 is performed by the signal processing unit 13. In Step T8, the correction coefficient (a) is calculated using the position information (x, y) and the correction magnetic field strength (M2) associated with the position information. More specifically, Step T8 includes Step T8a of acquiring an average value (Hm) of the correction magnetic field strength (M2), Step T8b of selecting the reference value (Href), and Step T8c of calculating the correction coefficient (a).

In Step T8a of acquiring the average value (Hm), the average value (Hm) of the correction magnetic field strength (M2) is acquired using the position information (x, y) and the correction magnetic field strength (M2) associated with the information (refer to Equation 1). Step T8a is performed by the memory 14 and the average strength acquisition unit 13b. For example, a case in which the average value (Hm) in the line L is calculated will be described as an example. A Y coordinate of the line L1 is 0. Therefore, the average strength acquisition unit 13b retrieves the correction magnetic field strength (M2) associated with the information of which the Y coordinate is 0 from the memory 14. The average strength acquisition unit 13b calculates the average value (Hm) of the retrieved correction magnetic field strength (M2). Step T8a of calculating the average value (Hm) is performed for each of the lines L1, L2, L3, L4, L5, L6 and L7 in which the correction magnetic field strength (M2) has already been acquired. Therefore, when the correction magnetic field strength (M2) is acquired for the seven lines L1, L2, L3, L4, L5, L6 and L7, the average strength acquisition unit 13b calculates seven average values (Hm).

[Math. 1]

$$(Hm)_n = \frac{\sum_{i=1}^{k}(M2)_i}{k} \quad (1)$$

Figure 7:
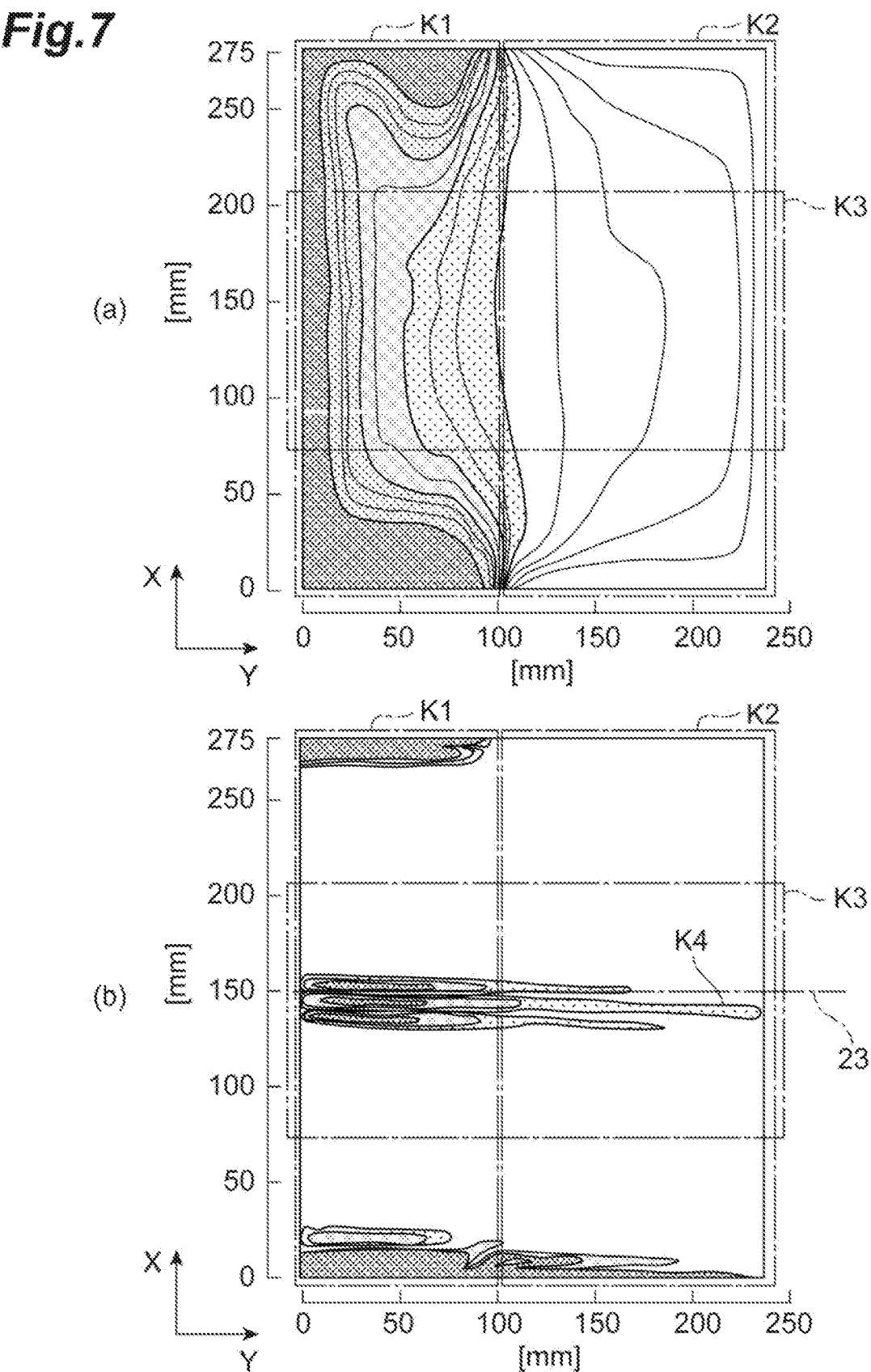
FIG. 7(a) is a diagram illustrating a magnetic field strength proportional to a current value generated in the test specimen illustrated in FIG. 6.
FIG. 7(b) is a diagram illustrating a magnetic field strength for detecting an arrangement disorder of carbon fibers occurring in the test specimen illustrated in FIG. 6.

(Hm)n: average value of the correction magnetic field strength in the $n^{th}$ line
M2: correction magnetic field strength
k: the number of samples for correction magnetic field strength
n: line number FIG. 7(a) is a contour diagram illustrating a distribution of a second magnetic field strength proportional to the current value in the test specimen S. The color contrast corresponds to a level of the current value. A dark portion is a portion in which the current value is relatively high. A faint portion is a portion in which the current value is relatively low. A region K1 is a region between the electrodes 9. As illustrated in FIG. 7(a), the current distribution in the test specimen S is not two-dimensionally uniform. Specifically, in the region K1 of the test specimen S, the current value changes in a direction from one electrode 9 toward another electrode 9 (that is, the set arrangement direction B). More specifically, a current value in the vicinity of the electrodes 9 tends to be larger than a current value in the vicinity of a center of a pair of electrodes 9. When the average value (Hm) is acquired, a range used for calculating the average value (Hm) is limited to a region (region K3) which does not include the region in the vicinity of the electrodes 9. That is, the average value (Hm) is calculated using the correction magnetic field strength (M2) obtained in the region K3. In other words, the correction magnetic field strength (M2) acquired in the region in the vicinity of the electrodes 9 which is not included in the region K3 is not used for calculating the average value (Hm).

The reference value (Href) is selected. In Step T8b, one reference value (Href) serving as a reference for correction is selected from seven average values (Hm). Step T8b is performed by the reference value acquisition unit 13c. For example, the reference value acquisition unit 13c selects a maximum value at a plurality of average values (Hm) as the reference value (Href). For example, when the current distribution in the test specimen S has a distribution as illustrated in FIG. 7(a), the reference value acquisition unit 13c selects the average value (Hm) in a region closest to a side edge as the reference value (Href). In other words, the reference value acquisition unit 13c selects the average value (Hm) of the line L1 as the reference value (Href). In short, the reference value acquisition unit 13c may select the average value (Hm) in a region in which the current value is relatively high in the test specimen S as the reference value (Href). The reference value acquisition unit 13c may select the reference value (Href) on the basis of other criteria.

In Step T8c of obtaining the correction coefficient (a), the correction coefficient (a) is calculated. Step T8c is performed by the acquisition unit 13d. Specifically, the acquisition unit 13d divides each of the plurality of average values (Hm) by the reference value (Href) (refer to Equation 2). The correction coefficient (a) is stored in the memory 14 in association with the number of the line L.

[Math. 2]

$$(a)_n = \frac{(Hm)_n}{Href} \quad (2)$$

(a)n: correction coefficient corresponding to the $n^{th}$ line
(Hm)n: average value corresponding to the $n^{th}$ line
Href: reference value Step T9 is performed. In Step T9, the detection magnetic field strength (M1) is corrected using the correction coefficient (a). Step T9 is performed by the signal correction unit 13e. The signal correction unit 13e retrieves the detection magnetic field strength (M1) and the correction coefficient (a) corresponding to the $n^{th}$ line L from the memory 14 using the position information (y) corresponding to the $n^{th}$ line L as a trigger. The signal correction unit 13e divides the detection magnetic field strength (M1) by the correction coefficient (a) (refer to Equation 3) and obtains a detection magnetic field strength M3 after the correction (first magnetic field strength after the correction). The division process is a correction process.

[Math. 3]

$$(M3)_n = (M1)_n \times \frac{1}{(a)_n} \quad (3)$$

(M3)n: detection magnetic field strength in the $n^{th}$ line after the correction
(M1)n: detection magnetic field strength in the $n^{th}$ line before the correction
(a)n: correction coefficient in the $n^{th}$ line By performing Steps T8a, T8b, T8c and T9, the corrected detection magnetic field strength (M3) in which a deviation in the current value is suppressed is obtained.

Step T10 is performed. In Step T10, an inspection for meandering is performed using the corrected detection magnetic field strength (M3). Step T10 is performed by the meandering inspection unit 13f. The meandering inspection unit 13f reads the corrected detection magnetic field strength (M3) from the memory 14. The meandering inspection unit 13f performs an inspection related to meandering. The inspection related to meandering includes a determination of the presence or absence of meandering and a determination of the position in which meandering occurs. The presence or absence of meandering may be determined according to a desired criterion. For example, as the desired criterion, a peak value at the corrected detection magnetic field strength (M3) can be adopted. In this case, when a magnetic field strength having wavelengths narrower than a predetermined threshold value and having an absolute value larger than a predetermined threshold value is detected, it may be determined that a change in the magnetic field M has occurred. When it is determined that a change in the magnetic field M has occurred, it is determined that meandering is present. Alternatively, when a waveform included in the corrected detection magnetic field strength (M3) is disordered and a magnitude of a deviation in a cycle of the waveform is equal to or larger than a predetermined threshold value, it may be determined that a change in the magnetic field M has occurred. When it is determined that the change in the magnetic field M has occurred, it is determined that meandering is present. The corrected detection magnetic field strength (M3) is associated with the position information (x, y). Therefore, a position in which meandering is present can be acquired by referring to the position information (x, y) corresponding to the information in which it is determined that meandering is present. Results of Step T10 are stored in the memory 14.

Step T11 is performed. In Step T11, the corrected detection magnetic field strength (M3) obtained by performing Step T9 and the result of the inspection related to the meandering obtained in Step T10 are displayed. Step T11 is performed by the display control unit 11a. When it is determined that there is no problem in the result, an installation position of the electrode 9 is changed (Step T12).

Hereinafter, a meandering detection direction and effects of the meandering detection device according to the present disclosure will be described.

FIG. 7(a) is a contour diagram illustrating the second magnetic field strength proportional to the current value on the main surface Sa of the test specimen S. The contrast of color corresponds to a level of the current value. A dark portion is a portion in which the current value is relatively high. A faint portion is a portion in which the current value is relatively low. FIG. 7(b) is a contour diagram illustrating the detection magnetic field strength (M1) on the main surface Sa of the test specimen S. The contrast of color indicates an intensity of the detection magnetic field strength (M1). A dark portion is a portion in which the magnetic field strength is relatively strong. A faint portion is a portion in which the magnetic field strength is relatively weak. FIG. 7(a) and FIG. 7(b) are results obtained in an example described later. A detailed explanation of the example from which FIGS. 7(a) and 7(b) are obtained will be described later.

For example, it may be assumed that a region in which meandering of the carbon fibers SE occurs extends in a direction (Y-axis direction) intersecting the set arrangement direction B. In this case, a disorder of the detection magnetic field strength (M1) occurs in the region in which meandering occurs. When a degree of meandering is constant in the direction (Y-axis direction) intersecting the set arrangement direction B, the magnetic field strength should also be constant with respect to the Y-axis direction. However, the magnetic field strength generated by meandering is not constant in the direction (Y-axis direction), like a region K4 illustrated in FIG. 7(b).

As illustrated in FIG. 7(a), this is because the current distribution in the test specimen S is not two-dimensionally uniform. Specifically, the current distribution in the direction (Y-axis direction) intersecting the set arrangement direction B in the test specimen S. Referring to FIG. 7(a), there is a current distribution in the Y-axis direction intersecting the set arrangement direction B. In the vicinity of one side edge, the current E flows linearly between one electrode 9 and another electrode 9, but the current E flows through a region K2 which is not between the electrodes 9 as it approaches the other side. Therefore, the current value is expected to be distributed in the Y-axis direction intersecting the set arrangement direction B.

Therefore, in the inspection method according to the present disclosure, attention is paid to the current value which varies in the direction (Y-axis direction) intersecting the set arrangement direction B. The magnetic field strength which can be quantitatively evaluated is obtained by correcting a change in the current value.

The arrangement of the carbon fibers SE may deviate from a preset arrangement direction. In this way, a state in which the actual arrangement direction of the carbon fibers SE deviates from the set arrangement direction is assumed to be a state in which the arrangement of the carbon fibers SE is disordered. When the current E is applied through the carbon fibers SE in Step T3 in which the current E is applied, the magnetic field M is generated. The magnetic field M is orthogonal to the direction in which the current E flows. Since the current E flows through the carbon fibers SE, the direction in which the current E flows coincides with the actual arrangement direction of the carbon fibers SE. Therefore, the magnetic field M is orthogonal to the actual arrangement direction of the carbon fibers SE. When the actual arrangement direction of the carbon fibers SE deviates from the set arrangement direction, the magnetic field M is inclined at an angle which is not orthogonal to the set arrangement direction. The magnetic field strength is affected by the current value.

Since the detection magnetic field measurement unit 6a is disposed so that the first detection axis D1 is parallel to the set arrangement direction, the detection magnetic field strength (M1) in the set arrangement direction is acquired. Therefore, since the magnetic field M is orthogonal to the set arrangement direction when there are no arrangement disorder of the carbon fibers SE, the detection magnetic field strength (M1) is zero. On the other hand, since the magnetic field M is inclined with respect to the set arrangement direction when there is an arrangement disorder of the carbon fibers SE, the detection magnetic field strength (M1) is a predetermined value. That is, according to Step T4a of acquiring the detection magnetic field strength (M1), the detection magnetic field strength (M1) including an influence due to an arrangement disorder of the carbon fibers SE and an influence of the current value is obtained.

Since the correction magnetic field measurement unit 6b is disposed so that the second detection axis D2 intersects the set arrangement direction, the correction magnetic field strength (M2) in the direction intersecting the set arrangement direction is obtained. The correction magnetic field strength (M2) is proportional to the current value. That is, according to Step T4b of acquiring the correction magnetic field strength (M2), the correction magnetic field strength (M2) including the influence of the current value is obtained.

In Step T10 of inspecting for meandering, the correction coefficient (a) is acquired using the correction magnetic field strength (M2). The correction coefficient (a) reduces the influence of the current value included in the detection magnetic field strength (M1). Therefore, the influence of the current value included in the detection magnetic field strength (M1) is reduced by correcting the detection magnetic field strength (M1) using the correction coefficient (a). Thus, according to Step T10, it is possible to reliably detect arrangement disorder of the carbon fibers SE.

Effects of the inspection method and the inspection device according to the present disclosure will be further described by an example being described. However, the inspection method and the inspection device according to the present disclosure are not limited to the following embodiment.

Figure 6:
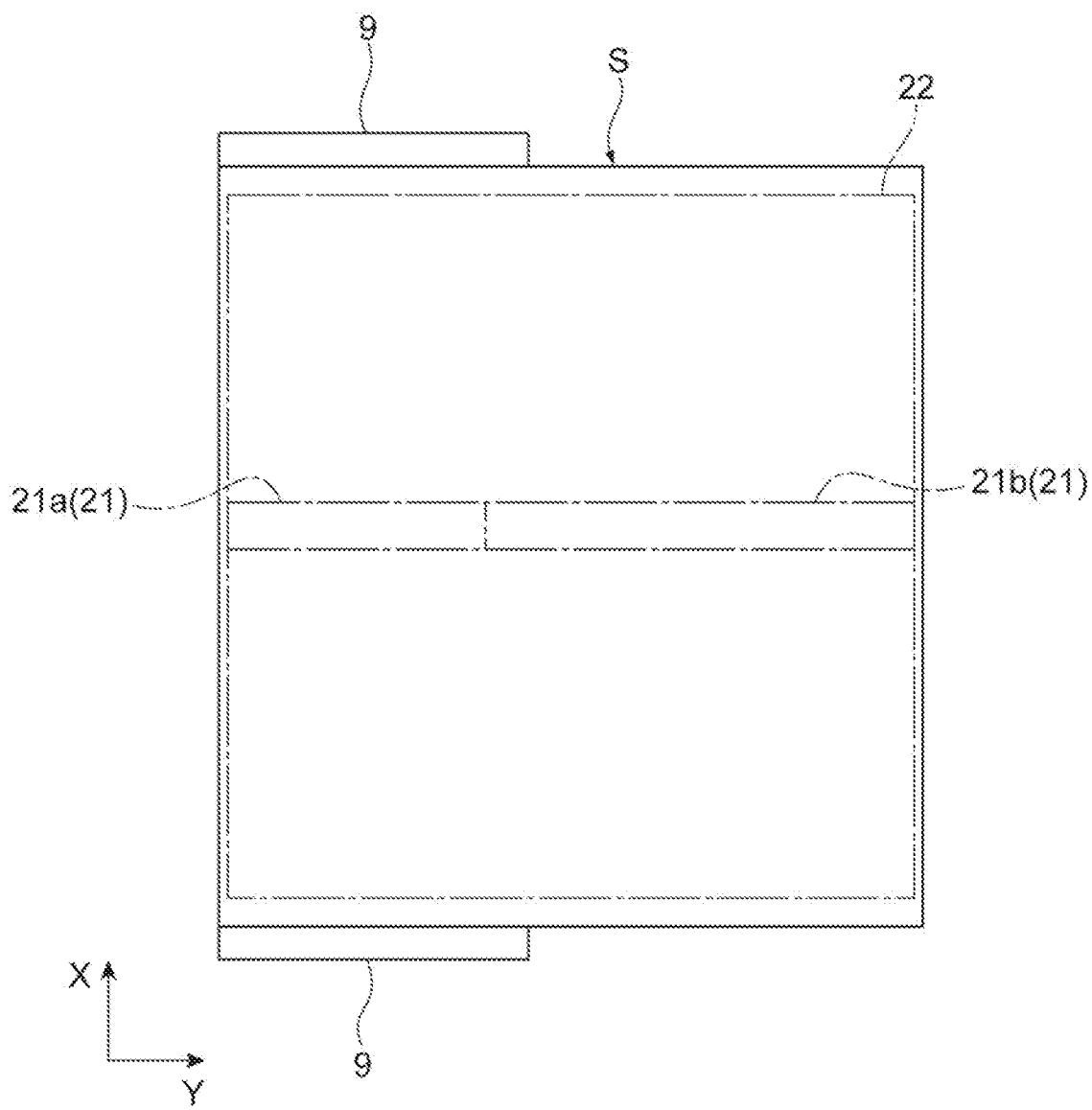
FIG. 6 is a diagram illustrating a test specimen according to an example.

In the embodiment, as illustrated in FIG. 6, a test specimen S in which meandering was intentionally introduced was prepared. The test specimen S was made of an electroconductive composite material. The test specimen S was a plate having 298 mm long (X-axis direction) and 235 mm wide (Y-axis direction). The test specimen S had a meandering introduction unit 21 extending in a width direction near an approximate center in a longitudinal direction. The meandering introduction unit 21 had a first region 21a and a second region 21b. The first region 21a was 90 mm wide. The first region 21a included several prepregs in which meandering was introduced. The second region 21b was 145 mm wide. Meandering layers in the second region 21b were less than those in the first region 21a. An inspection range 22 in the test specimen S had a rectangular shape. Specifically, the inspection range 22 in the test specimen S was 270 mm long and 235 mm wide. A pair of electrodes 9 was installed to fit the first region 21a in the longitudinal direction. A width of the electrodes 9 was 100 mm.

In the embodiment, an AMR sensor having two-detection axes which were X axis and Y axis was used as a magnetic field sensor. The current E supplied to the test specimen S at 100 kHz. The magnetic field sensor scanned along a trace as illustrated in FIG. 5. A scanning speed was 50 mm/sec. A scanning pitch in the longitudinal direction (X-axis direction) was 0.5 mm. A recording pitch in the width direction (Y-axis direction) was 1.0 mm.

FIG. 7(a) illustrates the distribution of the second magnetic field strength proportional to the current value. The contrast of color corresponds to a level of the current value. FIG. 7(b) illustrates the distribution of the detection magnetic field strength (M1). As illustrated in FIG. 7(a), it was found that the current value varied in the width direction (Y-axis direction) of the test specimen S. It can be understood that the detection magnetic field strength (M1) illustrated in FIG. 7(b) also varies in the width direction (Y-axis direction) of the test specimen S to correspond to the change in the current value (refer to a region K4).

Figure 8:
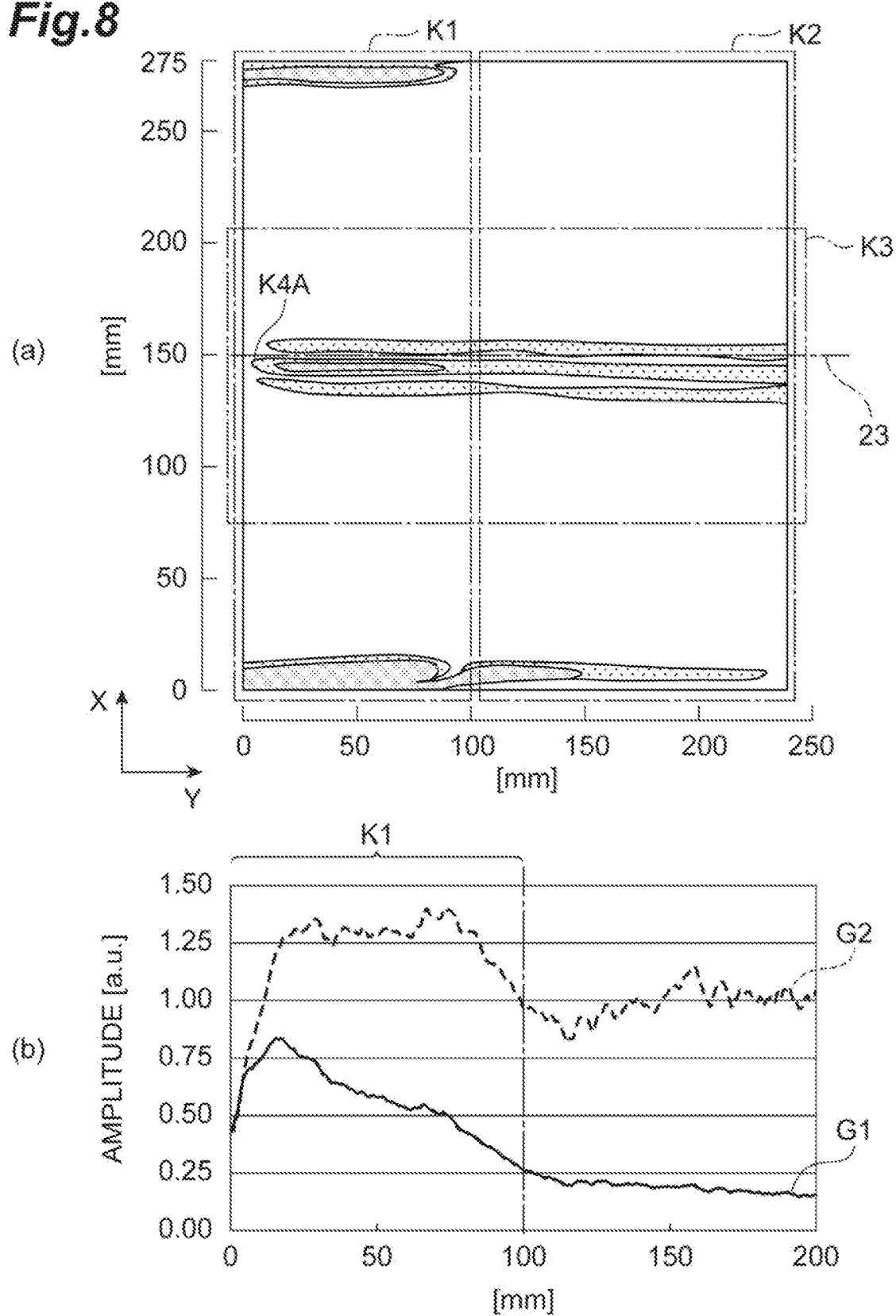
FIG. 8(a) illustrates results of correcting the magnetic field strength illustrated in of FIG. 7(b).
FIG. 8(b) is a diagram illustrating effects of the correction.

FIG. 8(a) illustrates a result of correcting the detection magnetic field strength (M1) illustrated in FIG. 7(b) using the inspection method according to the present disclosure. That is, FIG. 8(a) illustrates the corrected detection magnetic field strength (M3). As illustrated in FIG. 8(a), it can be understood that change in the width direction (Y-axis direction) is suppressed in a changing portion (region K4A) of the magnetic field indicating the presence of meandering. In FIG. 8(b), a graph G1 illustrates the distribution of the detection magnetic field strength (M1) before the correction in the region K4 of FIG. 7(b). A graph G2 illustrates the distribution of the corrected detection magnetic field strength (M3) in the area K4A of FIG. 8(a). In FIG. 8(b), a horizontal axis corresponds to the width direction of the test specimen S. The longitudinal axis corresponds to normalized amplitude. If the graph G1 before the correction is checked, it can be understood that the amplitude decreases in the width direction (Y-axis direction) of the test specimen S. A reduction in the amplitude corresponds to the current distribution. On the other hand, if the graph G2 after the correction is checked, it can be understood that the gradient for amplitude in the width direction (Y-axis direction) is reduced. Therefore, it was understood that the influence of the current value is reduced.

The present disclosure is not limited to the above-described embodiment.

In the test specimen S of the above-described embodiment, the plurality of prepregs (S1, S3, . . . , Sn−1), (S2, S4, . . . , Sn) having fiber arrangement directions differing by 90° from each other were alternately stacked. For example, in the test specimen, a plurality of prepregs having a fiber arrangement direction of plus or minus 450 may be alternately stacked. A plurality of prepregs in which the fiber arrangement directions are all in the same direction may be stacked on the test specimen S.

In the above-described inspection method, after the strength in the entire area of the test specimen S is acquired, strength processing is performed. For example, in the inspection method, the inspection processing may be performed whenever one strength history is acquired. In other words, the individual processes constituting the acquisition of the strength and the processing of the strength may be combined in a desired order.

INDUSTRIAL APPLICABILITY

According to the method and device for inspecting an electroconductive composite material of the present disclosure, it is possible to reliably detect arrangement disorder of the carbon fibers.

REFERENCE SIGNS LIST

1 Fiber meandering inspection device
2 Stage
3 Driver
4 Current applying device
6 Magnetic field sensor
6a Detection magnetic field measurement unit (first magnetic field measurement unit)
6b Correction magnetic field measurement unit (second magnetic field measurement unit)
7 Computer (data processing unit)
8 Lock-in amplifier
9 Electrode
11 Main control unit
12 Input/output unit
13 Signal processing unit
14 Memory
11a Display control unit
11c Stage control unit
11b Current control unit
12a Digitizer
12b Controller
13a Filter processing unit
13b Average strength acquisition unit
13c Reference value acquisition unit
13d Correction coefficient acquisition unit
13e Signal correction unit
13f Meandering inspection unit
B Set arrangement direction
C Actual arrangement direction
D1 First detection axis
D2 Second detection axis
E Current
Hm Average value
Href Reference value
M Magnetic field
M1 Detection magnetic field strength (first magnetic field strength)
M2 Correction magnetic field strength (second magnetic field strength)
M3 Corrected detection magnetic field strength S Test specimen
Sa Main surface
SE Carbon fibers
Sb One end
Sc Another end

The invention claimed is:

1. A method for inspecting an electroconductive composite material including carbon fibers, the method comprising:
disposing a first magnetic field measurement unit which acquires a magnetic field strength in a direction along a first detection axis so that the first detection axis is parallel to a set arrangement direction of the carbon fibers at a position facing a main surface of a test specimen including the electroconductive composite material;
disposing a second magnetic field measurement unit which acquires a magnetic field strength in a direction along a second detection axis so that the second detection axis intersects the set arrangement direction of the carbon fibers at the position facing the main surface of the test specimen;
applying a current between one end and another end of the test specimen via the carbon fibers;
acquiring a first magnetic field strength output from the first magnetic field measurement unit while relatively moving the first magnetic field measurement unit with respect to the main surface;
acquiring a second magnetic field strength output from the second magnetic field measurement unit while relatively moving the second magnetic field measurement unit with respect to the main surface; and
detecting a portion in which arrangement of the carbon fibers is disordered using the first magnetic field strength and the second magnetic field strength,
wherein the detection of the portion in which the arrangement of the carbon fibers is disordered comprises:
acquiring a correction coefficient which corrects the first magnetic field strength using the second magnetic field strength;
acquiring a corrected first magnetic field strength using the correction coefficient and
detecting the portion in which the arrangement of the carbon fibers is disordered using the corrected first magnetic field strength.

2. The method according to claim 1, wherein the acquiring of the correction coefficient comprises obtaining an average value of the second magnetic field strength, and calculating the correction coefficient using the second magnetic field strength and the average value.

3. The method according to claim 1, wherein, in the acquiring of the corrected first magnetic field strength, the first magnetic field strength is divided by the correction coefficient.

4. The method according to claim 2, wherein, in the acquiring of the corrected first magnetic field strength, the first magnetic field strength is divided by the correction coefficient.

5. A device for inspecting an electroconductive composite material including carbon fibers, the device comprising:
a first magnetic field measurement unit configured to acquire a magnetic field strength in a direction along a first detection axis and disposed so that the first detection axis is parallel to a set arrangement direction of the carbon fibers at a position facing a main surface of a test specimen including the electroconductive composite material;
a second magnetic field measurement unit configured to acquire a magnetic field strength in a direction along a second detection axis and disposed so that the second detection axis intersects the set arrangement direction of the carbon fibers at the position facing the main surface of the test specimen;
a current applying unit configured to apply a current between one end and another end of the test specimen via the carbon fibers;
a moving mechanism unit configured to relatively move the first magnetic field measurement unit and the second magnetic field measurement unit with respect to the main surface; and
a data processing unit configured to detect a portion in which arrangement of the carbon fibers is disordered using a first magnetic field strength output from the first magnetic field measurement unit and a second magnetic field strength output from the second magnetic field measurement unit,
wherein the data processing unit comprises:
a correction coefficient acquisition unit configured to acquire a correction coefficient which corrects the first magnetic field strength using the second magnetic field strength;
a signal correction unit configured to acquire a corrected first magnetic field strength using the correction coefficient and
a meandering inspection unit configured to detect the portion in which the arrangement of the carbon fibers is disordered using the corrected first magnetic field strength.

* * * * *